United States Patent [19]
Schatzmann et al.

[11] Patent Number: 5,832,411
[45] Date of Patent: Nov. 3, 1998

[54] AUTOMATED NETWORK OF SENSOR UNITS FOR REAL-TIME MONITORING OF COMPOUNDS IN A FLUID OVER A DISTRIBUTED AREA

[75] Inventors: Lawrence A. Schatzmann, Yorba Linda; James A. Wurzbach, Altadena; Russell R. Newcomb, Morgan Hill; David F. Ciambrone, Lake Forest, all of Calif.

[73] Assignee: Raytheon Company, El Segundo, Calif.

[21] Appl. No.: 794,389

[22] Filed: Feb. 6, 1997

[51] Int. Cl.$^6$ .................................................. G01N 27/26
[52] U.S. Cl. .............................. 702/23; 702/22; 702/30; 364/528.01; 204/406; 204/424; 422/83; 422/82.01
[58] Field of Search ..................................... 364/510, 509, 364/505, 506, 550, 551.01, 496.5, 564, 571.01, 571.03, 579, 580, 803, 569; 205/787, 775; 204/406, 408, 418, 429; 422/68.1, 82.01, 82.02, 83, 98, 70; 436/149–154; 73/31.01, 31.02, 31.06, 29.05, 23.2, 23.21–23.23, 23.31, 23.36, 23.4; 324/446, 691, 693; 340/603, 618, 620, 632–634

[56] References Cited

U.S. PATENT DOCUMENTS

| | | | |
|---|---|---|---|
| 5,106,756 | 4/1992 | Zaromb | 73/23.31 |
| 5,465,608 | 11/1995 | Lokshin et al. | 364/498 |
| 5,526,280 | 6/1996 | Consadoni et al. | 364/496 |
| 5,571,401 | 11/1996 | Lewis et al. | 205/787 |
| 5,610,835 | 3/1997 | Dominquez et al. | 364/371.01 |

*Primary Examiner*—Emanuel Todd Voeltz
*Assistant Examiner*—Hal P. Wachsman
*Attorney, Agent, or Firm*—Leonard A. Alkov; William C. Schubert; Glenn H. Lenzen, Jr.

[57] ABSTRACT

A plurality of sensor units are distributed over an area and communicate via a network with a central monitoring unit. The sensor units include sensor arrays that provide them with raw data in response to the presence of selected compounds in the ambient fluid. The raw sensor data is then processed to compute a local profile, which (a) illustrates a change in the compounds in the fluid from their normal state (change detection), (b) indicates the presence and total concentration of foreign compounds in the fluid (presence detection), or (c) details the composition and concentrations of defined classes or individual species of compounds in the fluid (composition detection). The local profiles from the individual sensor units are then used to compute a spatial and temporal map for the compounds in the fluid. This map can then be used for a variety of purposes including tracking and predicting the flow of compounds through the area, identifying the source of compounds in the area, monitoring abatement, and controlling industrial processes.

28 Claims, 5 Drawing Sheets

AUTOMATED NETWORK OF SENSOR UNITS FOR REAL-TIME MONITORING OF COMPOUNDS IN A FLUID OVER A DISTRIBUTED AREA

BACKGROUND OF THE INVENTION

1. Field of the Invention

This invention relates to sensing compounds in an fluid and more specifically to an automated network of sensor units, which are connected to respective sensor arrays, for monitoring the composition and concentration of compounds in a fluid over a distributed area in real-time.

2. Description of the Related Art

Air pollutant emissions are generated in such commercial settings as oil refineries, chemical plants, commercial paint spraying operations, and dry cleaner facilities. The oil refineries and chemical plants are characterized by large numbers of valves, flanges and fittings, each of which is a potential source of fugitive emissions. Typical facilities can have several hundred thousand of these devices, each of which is a potential source of a leak. Paint spraying and dry cleaning operations use chemicals in their processes, which pose a potential threat to employees and the surrounding environment. In each of these situations, it is important to measure both the composition and relative concentrations of the vapor levels in the surrounding environment in order to detect leaks in equipment, maintain a safe working environment, evaluate and maintain the efficiency of air filtering systems, and to safe guard the surrounding environment. Known vapor monitoring systems do not provide autonomous real-time and continuous data on a mixture of compounds in a gas or liquid medium at individual test points distributed over a wide area or piece of equipment, nor are they able to resolve the components of the mixture, i.e. its composition, and determine the concentrations of each component distributed over the area, track the vapor flow patterns, monitor the abatement of vapor levels, or predict the effects on the surrounding area.

The most common approach is for a technician to patrol the area with a handle-held sensor such as a flame ionization detector to detect the presence of fugitive emissions in the atmosphere. If the total level of emissions is too high, air samples are drawn into bags for subsequent analysis, e.g., by gas chromatography, to determine the precise composition and relative concentrations of the different emission compounds in the atmosphere at that location. This process is labor intensive and thus expensive, notoriously inaccurate due to the technician's inconsistency or inability to correctly position the sensor and then, if necessary, gather air samples for subsequent analysis, localized to each individual test site, involves a significant delay between data gathering and analysis, and is only performed occasionally. As a result, potentially dangerous levels of emissions can go undetected for long periods of time during which both people and the environment are exposed. Furthermore, during this delay, the source of the emissions may deteriorate further.

For example, in a large oil refinery valves may be checked as infrequently as once or twice a year. Thus, each leaky valve may be the source for considerable emissions in the atmosphere. Furthermore, if the valve continues to deteriorate if may present an explosion hazard. Similar hazards can occur in the paint spraying and dry cleaning operations if their air filtration systems should fail. Another drawback to this approach is that the collected data is highly localized and collected at different times, and therefore is not amenable to system level analysis.

Another less commonly used approach is to provide a heated plumbing network that draws vapor samples from each test point to a central unit. The heated plumbing is expensive to install and maintain, clutters the area, and introduces an inherent delay in the measurement due to the transit time of the sample from the test site to the central unit. Therefore, this configuration has limited utility in monitoring large areas such as typically found in oil refineries and chemical plants.

Another type of centralized system uses a laser to sweep the area. The laser excites spectroscopic transitions in plume constituents, which can be detected back at a central receiver using a spectrometer. This technique provides for a measure of classification and a certain level of quantification as well, but it is not applicable to monitoring a field of test points. Laser systems are designed for sweeping the air over a wide region in search of pollutant plumes but cannot target a multitude of specific test points such as individual valves in a refinery or process points in a manufacturing facility. Furthermore, even though lasers can be operated safely in this application, a neighboring community may object to the laser scanning.

Recently a number of organic polymer based sensors have been developed for the purpose of sensing fugitive emissions, U.S. Pat. No. 5,417,100 Reversible Sensor for Detecting Solvent Vapors to Miller, European Patent No. 0 596 973 B1 Device for Sensing Volatile Materials to Gardiner, and U.S. Pat. No. 5,571,401 Sensor Arrays for Detecting Analytes in Fluids to Lewis. These sensors are cheaper than flame or photo ionization detectors, operate at lower power levels, and facilitate passive sensing. The patents suggest that these sensors may be used either individually or in arrays, in which the individual sensor elements have a predetermined intersensor variation such that different vapor compounds exhibit unique response signatures in a hand held or localized emissions sensing system.

For example, Miller shows an alarm system that comprises a single sensor linked to a computer, which monitors the sensor's response level and, when appropriate, activates an alarm. Gardiner teaches a centralized unit that uses a single sensor array to sense and classify the different aromas of various beers and the variations in aromas of the same beer stored in different manners. In this case, the source of emissions (the beer) is brought to the sensor unit. This is not practical or even possible to do in most industrial settings. Lewis teaches a hand-held electronic nose for detecting fugitive emissions, which is constructed by using a single array, which often has at least one thousand different sensors and up to one hundred thousand sensors, in conjunction with an electrical measuring device for measuring the response of each sensor. The electronic nose can be used in much the same manner as the hand-held flame ionization detector.

There remains a need for an autonomous system that provides real-time and continuous monitoring of the vapor composition and relative concentrations at a large number of test points distributed over a wide area, and which is capable of estimating the vapor composition and concentrations over the entire area and tracking and predicting their flow patterns.

SUMMARY OF THE INVENTION

In view of the above problems, the present invention provides an automated and real-time system for monitoring compounds in a fluid at multiple points distributed over an area of interest and computing their spatial and temporal properties.

This is accomplished by distributing a plurality of sensor units over an area, which communicate over a network with a central monitoring unit. The sensor units include sensor arrays that provide them with raw data in response to the presence of selected compounds in the ambient fluid. One or more environmental sensors may be used to sense the local environmental conditions, which can then be used to compensate the raw sensor data so that it accurately reflects the properties of the compounds in the fluid, and not variations in the environmental conditions. The raw or compensated sensor data is then processed to compute a local profile, which (a) illustrates a change in the compounds in the fluid from their normal state (change detection), (b) indicates the presence and total concentration of foreign compounds in the fluid (presence detection), or (c) details the composition and concentrations of defined classes or individual species of compounds in the fluid (composition detection). The local profiles from the individual sensor units are then used to compute a spatial and temporal map for the compounds in the fluid. This map can then be used for a variety of purposes including tracking and predicting the flow of compounds through the area, identifying the source of compounds in the area, monitoring abatement, and controlling industrial processes.

These and other features and advantages of the invention will be apparent to those skilled in the art from the following detailed description of preferred embodiments, taken together with the accompanying drawings, in which:

DETAILED DESCRIPTION OF THE INVENTION

Figure 1:
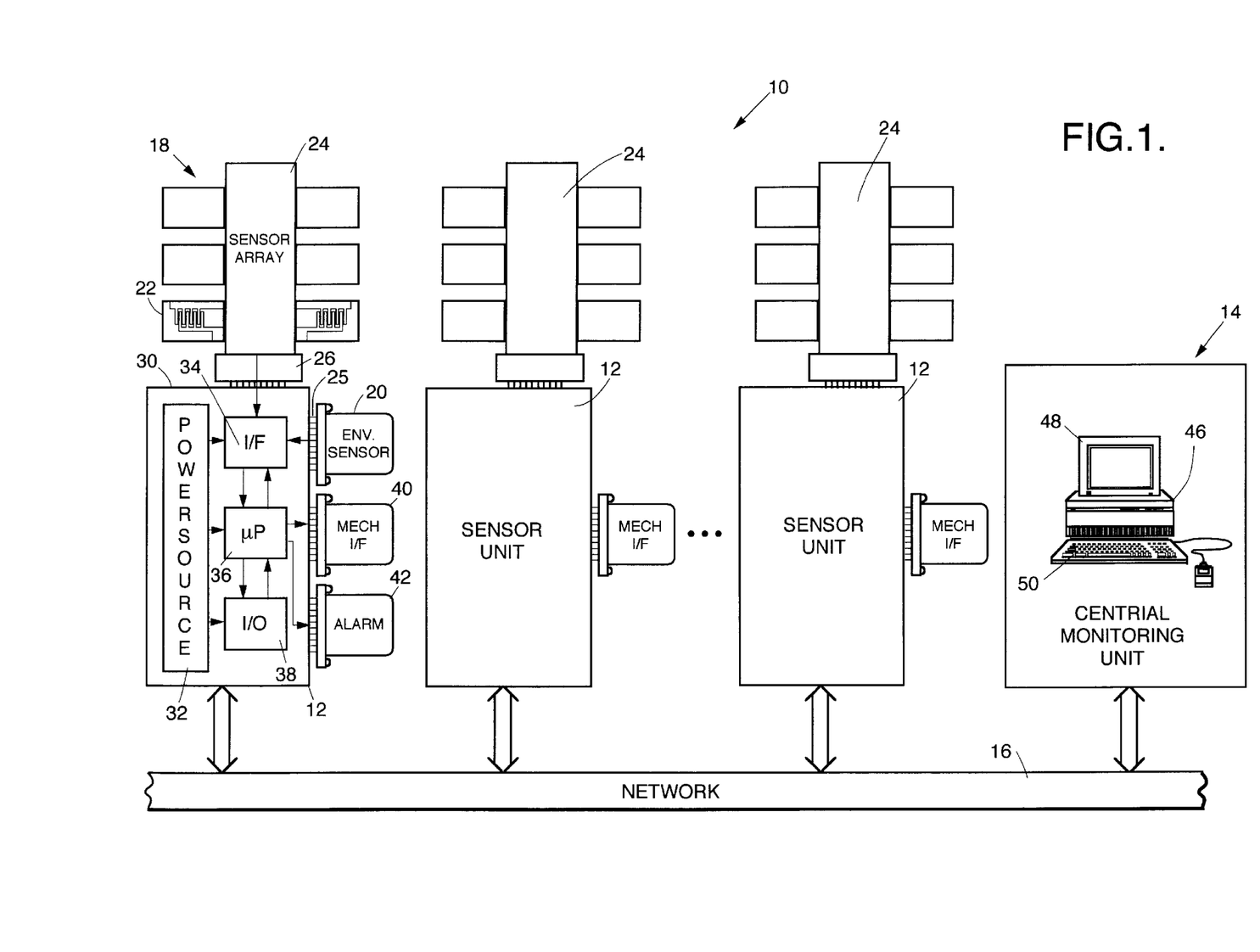
FIG. 1 is a block diagram of a network of vapor sensor units in accordance with the present invention.

The present invention provides an automated and real-time system for monitoring compounds in a fluid at multiple points distributed over an area of interest and computing their spatial and temporal properties. As shown in FIG. 1, the monitoring system 10 includes a plurality of sensor units 12 that are distributed over the area of interest and a central monitoring unit 14 that is positioned at a central location. The sensor units 12 and central monitoring unit 14 communicate over a network 16 such as hard wired, RF, microwave or optical networks. A plurality of sensor arrays 18 are coupled to the respective sensor units 12 and provide them with raw data in response to the presence of selected compounds in the ambient fluid. The sensor units 12 optionally include one or more environmental sensors 20 for sensing the local environmental conditions including temperature, humidity, pressure and wind conditions. This information can then be used to compensate the raw sensor data so that it accurately reflects the properties of the compounds in the fluid, and not variations in the environmental conditions.

The raw or compensated sensor data is then processed to compute a local profile, which (a) illustrates a change in the compounds in the fluid from their normal state (change detection), (b) indicates the presence and total concentration of foreign compounds in the fluid (presence detection), or (c) details the composition and concentrations of defined classes or individual species of compounds in the fluid (composition detection). The local profiles from the individual sensor units 12 are then used to compute a spatial and temporal map for the compounds in the fluid over the area of interest. This map can then be used for a variety of purposes including tracking and predicting the flow of compounds through the area, identifying the source of compounds in the area, monitoring abatement, and controlling industrial processes.

This processing can be done locally in the individual sensor units 12, in which case the system's computational capability is distributed throughout the network and the central monitoring unit 14 is used only to monitor the results. Conversely, the sensor units 12 can transmit the raw data to the central monitoring unit 14, which then computes the local profiles for each sensor unit 12 and interrelates the data to compute the spatial and temporal map. The precise allocation of the computational resources will depend on the particular application. For example, the simplest and cheapest sensor units would simply measure the raw data and transmit it to the central monitoring unit 14. The main drawback to this approach is that the traffic on the network 16 is high. Another approach is to provide each sensor unit 12 with enough processing capability to compute its own local profile, which is then transmitted over the network 16 to the central monitoring unit 14, which then interrelates the different local profiles to compute the spatial and temporal map. This approach reduces the traffic on the network 16 but increases the complexity and cost of the individual sensor units.

The sensor arrays 18 can be designed to detect the presence of volatile organic compounds (VOCs), inorganic vapors, fog, aerosols, smoke or water. The sensitivity of the sensor arrays and the sophistication of the signal condition can be designed to identify different classes of, for example, VOCs such as Ketones, Benzene-Toluene-Ethyl Benzene-Xylene (BTEX), Acetates, Alcohols, and Aliphatic Hydrocarbons, or individual species within, for example, the BTEX class of VOCs such as Xylenes, Toluene and Ethyl Benzene. In many applications, the compounds are vapors that are suspended in the ambient atmosphere (the fluid). In other applications, the fluid itself may be a compound such as nitrogen $N_2$ or may be a liquid such as water.

The simplest sensor array 18 includes a single sensor element 12 such as the organic polymer based sensor described by Miller in U.S. Pat. No. 5,417,100. Under normal ambient conditions, whatever they may be, the single sensor element 22 outputs a constant baseline response such as a constant current. If the conditions in the fluid should change, either through the introduction of a new foreign compound or a change in concentration of the existing compounds, the sensor element 22 will sense that change and vary its output response. The identification of the compound and its concentration are reflected by how fast and how much the element's response changes. However, in a single sensor element array the amount of information detected is only sufficient to determine whether a significant change in the ambient conditions has occurred or to determine whether a foreign compound is present.

In applications in which is it necessary or desirable to ascertain the composition and concentrations of defined classes of compounds or individual compound species, the sensor array 18 includes a plurality of sensor elements 22 that are mounted on a substrate 24. The substrate can be either a rigid planar member or a flexible member that conforms to the shape of the desired application. The sensor elements 22 are designed so that each of them responds to the same compound with a slightly different sensitivity. The intersensor deviations allow each array 18 to distinguish between different classes or species and to detect their respective concentrations with reasonable accuracy. This can be accomplished by using a plurality of Miller's polymer sensors with slightly different designs in conjunction with the signal conditioning algorithm described in FIG. 3 herein or, alternately using the sensor arrays and processing described by Lewis in U.S. Pat. No. 5,417,100. The sensor arrays are not limited to polymer sensor but may include metal oxide sensor elements or a hybrid of polymer and metal oxide sensor elements.

The specific design of sensor units 12 depends upon the particular application in which they will be used. As shown in FIG. 1, the sensor units 12 include an external connector 26, which provides a electro-mechanical coupling to the sensor array 24 that projects it out into the environment being sampled. Performance degradation of the sensor elements over time is further exacerbated by the direct exposure of the sensor array to the surrounding environment. Therefore, the external connector 26 preferably allows the sensor array to be easily detached and replaced with a new array.

In this configuration, the sensor array 24 passively samples the compounds in the fluid around the sensor unit. Passive sampling is governed by diffusion and/or the movements of compounds in the fluid around the sensor array. Other examples of passive sampling mechanisms include a) an enclosure around the sensor array having openings through which the fluid can be sampled and b) a gas permeable barrier that protects the sensor elements while allowing the compounds in the fluid to permeate therethrough to the sensor elements. Passive sampling mechanisms are generally less complex and less expensive than active sampling mechanisms of the type shown in FIG. 2 but provide less flexibility and control over the sampling process.

The sensor units 12 also include an external connector 28 for electro-mechanically coupling environmental sensors 20 to the sensor unit. Because the sensor array 24 is directly exposed to the environment around the sensor unit 12, the environmental sensors 20 measure the conditions such as temperature, humidity and pressure in the same environment. This information is used to compensate the raw sensor data so that it accurately reflects the properties of the compounds in the fluid and not variations in the environmental conditions.

The sensor units 12 further include an enclosure 30 that houses a power source 32 such as batteries, solar cells, a connection to a local power grid or any other means of supplying power to the sensor array 24, the environmental sensors 20 and the sensor units' internal circuitry. The sensor unit may include power management capabilities such as power conditioning, power storage or duty cycling. An interface 34 selectively samples the raw sensor data from each of the sensor elements 22 and the environment sensors 20, multiplexes the data, and converts it into a digital data stream. In its simplest configuration, a microprocessor 36 formats the digital data stream into an output data stream that can be transmitted over the network. In this case, an I\O circuit 38 places the output data stream onto the network 16 for transmission to the central monitoring unit 14.

Alternately, the microprocessor 36 can filter the raw data from the sensor array and environmental sensors to reduce noise, compensate the raw sensor data from the sensor elements 22 in accordance with the sensed environmental conditions, and then compute the local profile, which is then placed on the network by the I\O circuit 38.

Figure 2:
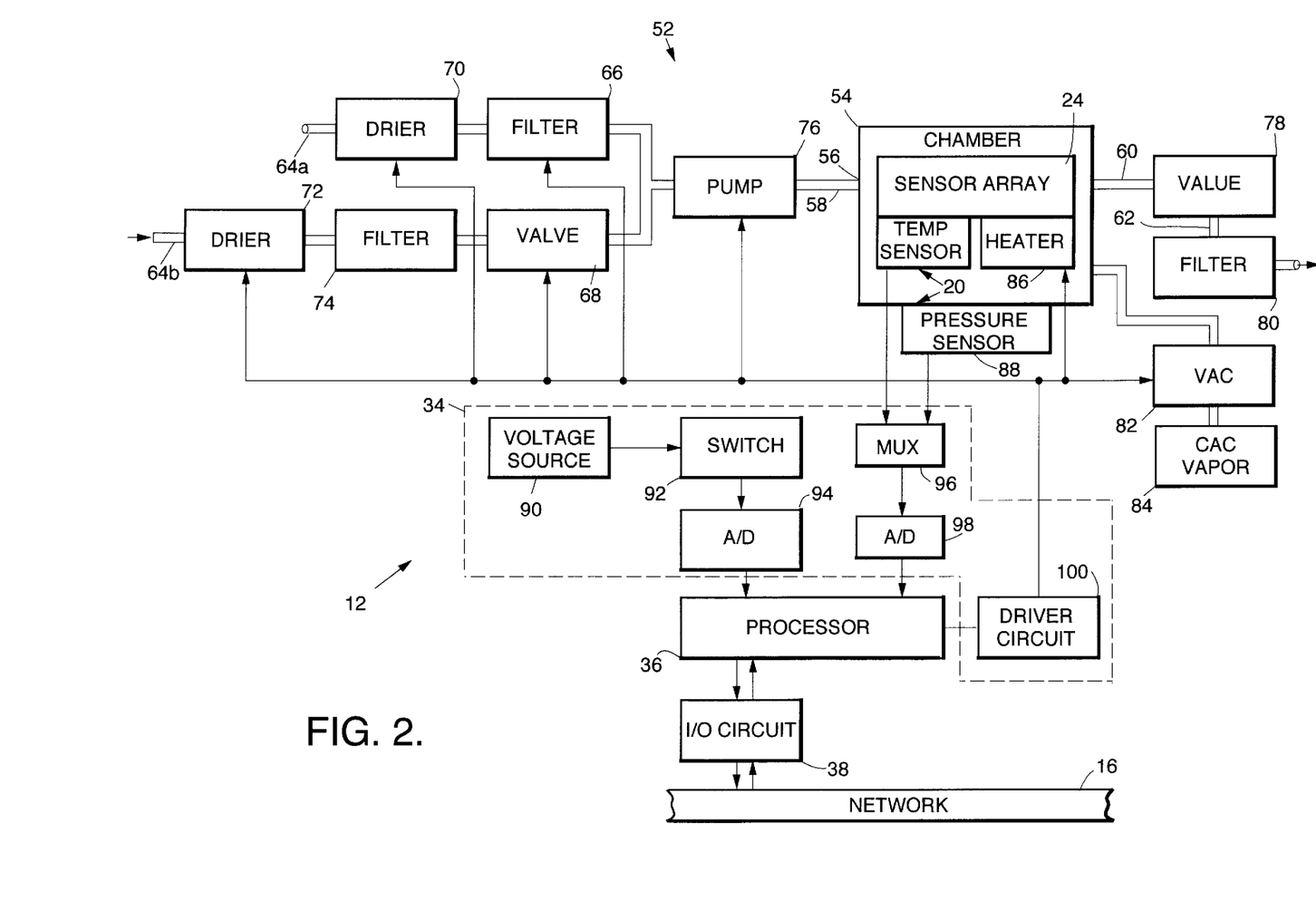
FIG. 2 is a block diagram of one embodiment of the sensor unit shown in FIG. 1.

The sensor unit 12 can also be designed to perform a number of other tasks, either independently or in conjunction with the central monitoring unit 14. For example, depending upon the type of sensor elements employed and the nature of the fluid and compounds to be monitored, the sensor unit may have to condition, treat, activate or develop the sensor elements 22 before and/or after exposure to the fluid. In this case, the sensor unit would include additional apparatus such as spray heads, immersion containers, dryers or actuators for delivering or removing fluids to and from the sensor element. In addition, the sensor unit 12 may include a capability for sensor calibration. In this case, the sensor unit would include additional apparatus, such as shown in FIG. 2, to isolate the sensor array from the environment being sampled and expose the sensors to a known calibration fluid. The difference between the calibration fluid's profile and the computed local profile is then used to adjust the parameters in the signal conditioning algorithm. The sensor unit may also include a capability for self test, in which it checks for connectivity, status of the different sensors, readiness and calibration.

The sensor units 12 may also have the capability of taking remedial or corrective action. For example, a mechanical interface 40 such as a switch, an actuator, or a valve may be connected between the sensor unit 12 and a piece of industrial equipment and have the capability of adjusting or even shutting down the operation of that piece of equipment in response to the sensor unit's local profile or conditions elsewhere in the area. The sensor unit 12 may also be provided with an alarm 42, which may be activated in response to the unit's local profile or in anticipation of a problem based upon the area's spatial and temporal map.

The central monitoring unit 14 has an I\O port for interacting with the network, a processor 46 for processing the data from the several sensor units 12, a display 48 for displaying the relevant information for a particular process such as the presence of high concentrations of certain compounds in the different local areas, substantial changes in compound levels, flow patterns of compounds through and outside the area, predicted flow patterns or problems that may occur, the status of an abatement process, or processing control parameters, and a user interface 50, e.g. a keyboard that allows a technician to interact with the system. Depending on the allocation of the computational capability throughout the network, the processor 46 may simply control the presentation of the local profile information and spatial and temporal map information on the display 48. Alternately, the central monitoring unit may perform all the processing to compute each of the local profiles, the spatial and temporal map, and any flow patterns, predictions, processing control analysis or source identification.

The central monitoring unit 14 may also have the capability of taking corrective action. For example, the processor may display a warning message to the technician, warning him of a sensor unit failure, an impending failure or dangerous levels of toxic compounds in the environment and may further describe the necessary corrective action that needs to be taken. Alternately, the central monitoring unit may take the necessary action itself. For example, it may sound an alarm, adjust an industrial process, shut down a valve, or direct a particular sensor unit to recalibrate itself. The amount of automation will depend on the specific application.

The described monitoring system 10 can be used in many different applications. For example, the sensor units can be distributed across an oil refinery to monitor the leakage of VOCs into the atmosphere. As a result, a valve failure will be discovered immediately and a technician dispatched before it can present a serious safety hazard or seriously impact the operation of the refinery. Furthermore, the data gathered can be used to predict impending valve failures and thus fix them before failure occurs. The system can also be used to monitor emission levels from industrial plants such as chemical or textile facilities. The data gathered can then be used to track and predict the progression of the plume over time. In cases of an industrial incident, this information can be used to first warn downwind populations and later to estimate the impact of the incident on those environments. Where there are a number of possible offending industrial facilities, the information can be used to identify the source of the emissions. In many industrial facilities that produce dangerous compounds, processes are used to destroy those compounds or convert them into benign compounds before the fluid is discharged back into the atmosphere. In this case, the network of sensor units can be used to monitor the destruction efficiency of the process and to suggest and/or take corrective action to maintain performance efficiency.

FIG. 2 illustrates a particular embodiment of the sensor unit 12 that includes an active vapor sampling mechanism (VSM) 52 for sensing vapors such as VOCs in the ambient atmosphere. The active VSM 52 provides greater control and flexibility over the vapor sampling process than does passive sampling, which facilitates calibration of the sensor elements and direct environmental compensation. The VSM 52 includes a chamber 54 for enclosing the sensor array 24 in a controlled environment. The chamber 54 includes an inlet 56 that receives sampled air from the ambient atmosphere through a sampling tube 58 and an outlet 60 that vents the sampled air back to the ambient atmosphere through a duct tube 62.

The sampling tube 58 preferably has dual intake paths 64a and 64b that are respectively provided with intake valves 66 and 68 to selectively draw air from the ambient atmosphere. Optionally, the intake paths may include driers 70 and 72 for controlling the humidity and pressure of the sampled air. Intake path 64b is further provided with an active carbon filter 74 that neutralizes the VOCs in the sampled air such that the filtered air represents the underlying fluid or atmosphere absent the VOC emissions. Conversely, the sampled air drawn through intake path 64a includes both the atmosphere and the VOC emissions. An air pump 76 is interposed between the valves 66, 68 and the inlet 56 to chamber 54 to selectively draw air from the external atmosphere through intake paths 64a and 64b into the chamber. A check valve 78 is placed in the duct tubing 62 to control the evacuation of the chamber. An active carbon filter 80 can be placed in the duct tubing 62 to remove the VOCs from the sampled air before it is returned to the ambient atmosphere.

To sample the atmosphere values 66 and 68 are closed and check valve 78 is open to evacuate the chamber 54. Once evacuated, check value 78 is closed and one of the valves 66 or 68 is opened so that the pump 76 draws air through the selected intake path to fill the chamber 54. Once filled, that valve is also closed. At this point, the interface circuit 34 samples the responses from the sensor array's individual sensor elements. After one or more sampling cycles, the intake valve is closed and the check valve 78 is opened to evacuate the chamber.

To obtain accurate results, the monitoring process must be periodically calibrated to compensate for degradations in the sensor elements, variations in the fluid, and changes in the environmental conditions. Temporal changes in the performance of the sensor elements are compensated for by exposing the sensor elements to a calibration vapor. This is accomplished by first evacuating the chamber and then opening a check valve 82 to draw calibration vapor 84 into the chamber. The computed local profile is then compared to the calibration vapor's known profile and the error is used to adjust computational parameters in the signal conditioning algorithm. Changes in the fluid itself are detected by periodically opening intake valve 68 thereby drawing filtered air into the chamber. Changes in the resulting profile indicate temporal changes in the fluid outside the sensor unit.

Variations in the environmental conditions inside the chamber can effect the response of the array's sensor elements. The environmental conditions inside the chamber can either be measured and compensated for using signal processing techniques or they can be maintained in a relatively constant state. This particular sensor unit directly controls the environmental conditions in the chamber. A temperature sensor 20 measures the temperature of the sensor array. The processor 36 uses this information to control a heater 86 that adjusts the temperature of the solar array 24. A pressure sensor 88 measures the pressure inside the chamber 54. The processor controls driers 70 and 72 to adjust the pressure in the chamber 54 and the humidity of the sampled air.

In this embodiment, the interface circuit 34 includes a voltage source 90 that controls an n-to-1 analog switch 92 that cyclicly samples each of the n sensor elements in the sensor array 24 and outputs an analog voltage level that is proportional to the response of the sampled sensor element. The voltage source 90 may be either DC or AC depending upon the application. DC sources are simpler and somewhat cheaper whereas AC sources mitigate baseline variations due to such effects as polarization and ion drift. An analog-to-digital converter 94 converts the analog voltage level into a digital signal, suitably 20 bits per sample, which is input to the processor 36. A multiplexer 96 samples the different analog voltage signals produced by the temperature and pressure sensors to produce a single analog voltage signal. An analog-to-digital converter 98 converts the analog voltage signal into a digital data stream that is applied to the processor 36.

The processor 36 issues control signals to control the operation of the active vapor sampling mechanism 52 and, in response to the sensed environmental conditions inside the chamber, to control the operation of driers 70 and 72 and heater 86. A driver circuit 100 generates an analog voltage signal in response to the digital control signal and applies it to the specified element to either facilitate a sampling cycle or compensate for the environmental conditions. The processor 36 processes and formats the data as discussed previously and I/O circuit 38 places it on the network 16. The IO circuit 38 can also read data off the network such as directions from the central monitoring unit to initiate calibration or self test.

Figure 3:
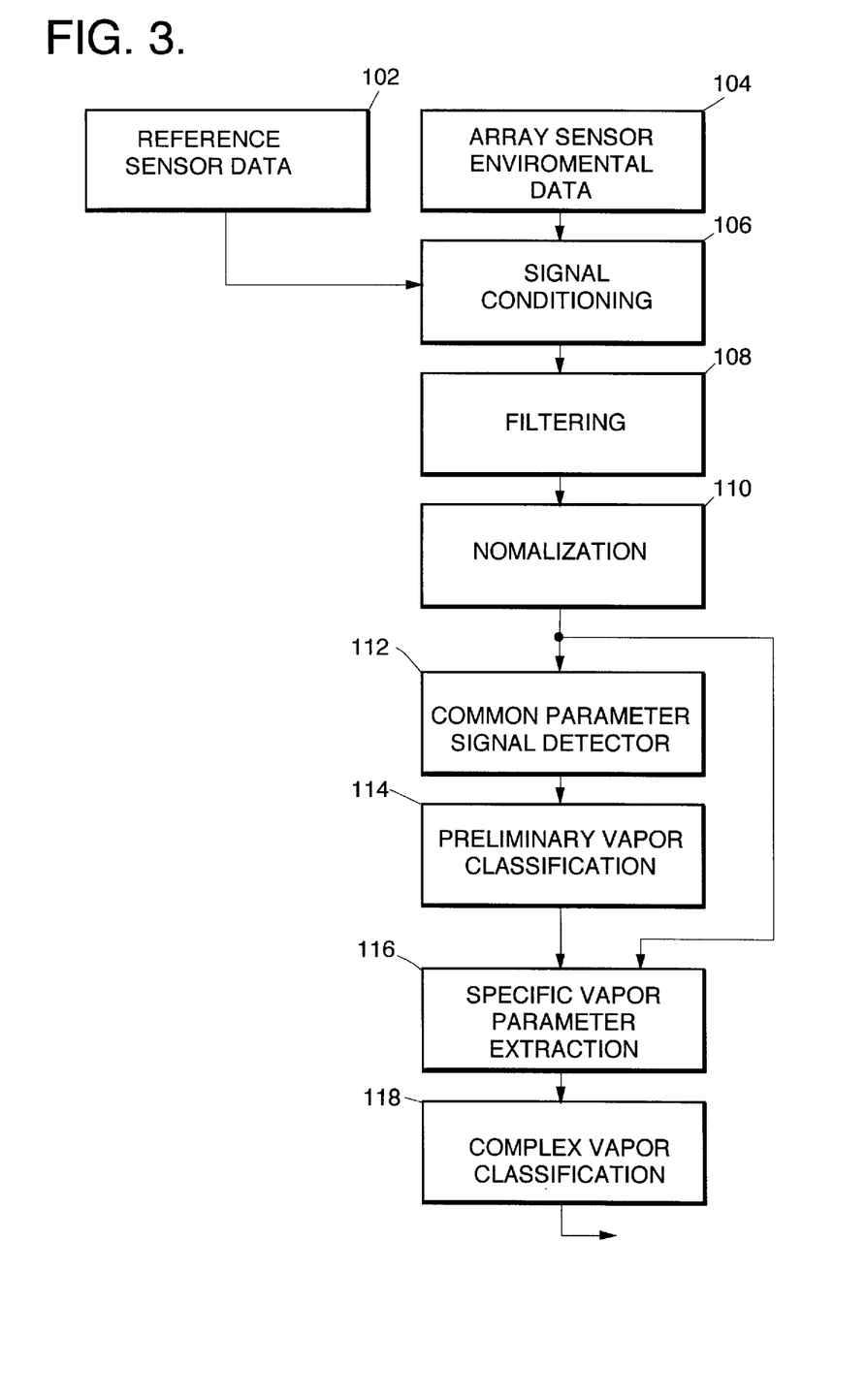
FIG. 3 is a flowchart of the signal conditioning algorithm for computing the vapor composition and their concentrations from the raw sensor data.

FIG. 3 illustrates one method for processing the raw sensor data produced by the sensor array to compute the composition of the compounds in the fluid and their concentration levels. The reference array sensor data (step 102) and array sensor data and environmental data (step 104) are gathered by opening valves 68 and 66, respectively, as shown in FIG. 2, digitized and passed to the signal conditioning module (step 106). The signal conditioner validates the array measurements and corrects data errors such as dropouts, outliers, and defective sensor element responses. The signal conditioner also compensates for environmental conditions according to the reference sensor measurements. The error signal generated during calibration is then used to adjust the sensor response levels. The resulting conditioned signals are passed to the filtering module (step 108) where background drift and specific noise conditions are rejected using conventional digital filters. Although filtered, the output of the filtering module necessarily contains noise that shares common features with the desired sensor signals. The filtered output is passed to the sensor response normalizer (step 110), which converts the raw measurement data into a percent change, consistent with the behavior of polymer sensors.

The normalized measurements are then passed to a common parameter signal detection module (step 112). Since the compounds present are at this point unknown, each sensor element's response is compared to the response models of the expected vapor compounds, e.g. the responses may be correlated with compound response models in a parallel bank of matched filters. Each model is optimized to uniformly weight the sensor responses across the various expected compounds. The module outputs the likelihood that each compound is present at each sensor element and a preliminary estimate of the vapor concentration for each compound. A preliminary vapor classification module (step 114) combines the individual sensor element statistics from the previous module across the sensor array to produce a composite likelihood that any of the expected compounds are present. This can be accomplished using any of several methods such as a Bayesian model or principal component analysis. The classification statistics are then recast in terms of detection and false alarm probabilities so that a statistical threshold may be used to declare whether or not each compound is present.

A specific vapor parameter extraction model (step 116) coherently executes a refined correlation process on the original normalized data across all sensor elements in the array using a response model that is based on the detected compound. Assuming that the identification of the compound is correct, this provides an optimal estimate of the vapor concentration levels. A complex vapor classification model (step 118) processes mixtures of compounds in the same manner by using the linearity of combined responses that characterizes the sensor elements. This module outputs the final estimates of the compounds that are present, i.e. the composition, the concentration levels and their error variances.

Figure 4:
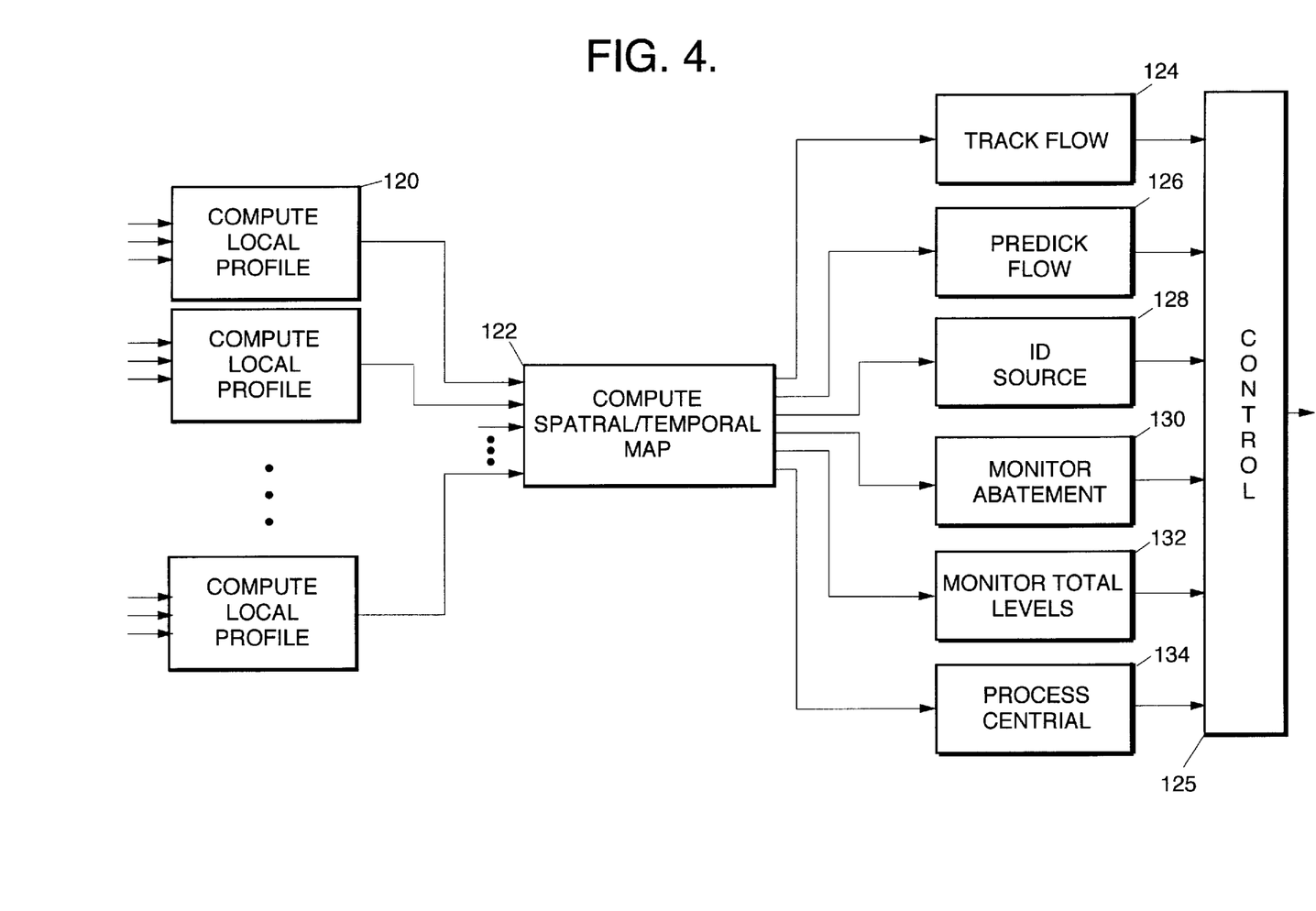
FIG. 4 is a flowchart illustrating various system level processes available to the central monitoring unit shown in FIG. 1.

FIG. 4 is a flow chart illustrating the real time processing capabilities of the present monitoring system. The raw sensor data gathered at each sensor unit is processed to form a plurality of local profiles (step 120). As discussed previously, the local profile may indicate a significant change in the fluid, mark the presence and total concentration of foreign compounds in the fluid, or specify the composition and concentration levels of the compounds. Thereafter, the local profiles of the different sensor units are interrelated to define a spatial and temporal map (step 122). The content of the spatial/temporal map depends both on the specific application and the content of the local profiles. For example, the map may show the current composition and concentration levels at each sensor unit as well as the change or trend over a period of time.

Because the several local profiles and the spatial/temporal map represent information simultaneously gathered over a wide area and processed in real-time, they can be used to perform different application specific functions. For example, sensor units can be distributed around an industrial facility that emits a plume of vapors into the atmosphere. The spatial/temporal map can be used to track the flow (step 124) of vapors across the area covered by sensor units. This data can be used to control (step 125) the operation of the facility or abatement equipment, warn downwind populations, or analyze the effect of exposure on the environment. The flow patterns inside and outside the area can be predicted (step 126) by using the flow information, wind speed/direction, and a kinetic model of the natural decomposition of the target vapors subjected to a fluid dynamic analysis. Predicted flow patterns can be used to predict potential equipment failures or dangerous levels of vapors and then issue a warning signal. If there were several industrial facilities in the vicinity that could be the source of the emissions, the spatial/temporal map can be subjected to a gradient analysis, which would reveal increasing concentration levels leading back to the source of the discharge (step 128).

The system can also be used to monitor the abatement (step 130) of emissions from a source. For example, some industrial processes generate waste materials that produce emission levels that generally start off high and decrease with time. These types of wastes can be placed in sealed monitor wells below ground until they are safe for permanent disposal. A three-dimensional matrix of sensor units can be placed in the well to monitor the composition and concentration of the emissions over time. This provides a technician with a three-dimensional view of the progress of the abatement process. Instead of monitoring the specific composition and concentration levels, the system may only provide the total concentration (step 132) of target emissions in the atmosphere. For example, in a refinery each sensor unit may be used to detect whether a certain valve or actuator is leaking. If the total concentration of target emissions exceeds some threshold, then the sensor unit flags it as faulty.

In order to ensure the safety of workers and the surrounding environment, facilities that produce fugitive emissions are typically required to monitor those initial levels, convert and/or destroy the emissions into benign compounds, and report the residual emissions level released back into the atmosphere. The sensor units of the present invention can be distributed throughout the facility to measure the initial emissions, monitor the performance of the abatement process, and detect the released levels. This information is then reported to the central monitoring unit, which can use the data to adjust the abatement process to meet pollution requirements, sound an alarm and/or vent the contaminated air directly to the atmosphere if it endangers people, and record violations of emissions standards.

Figure 5:
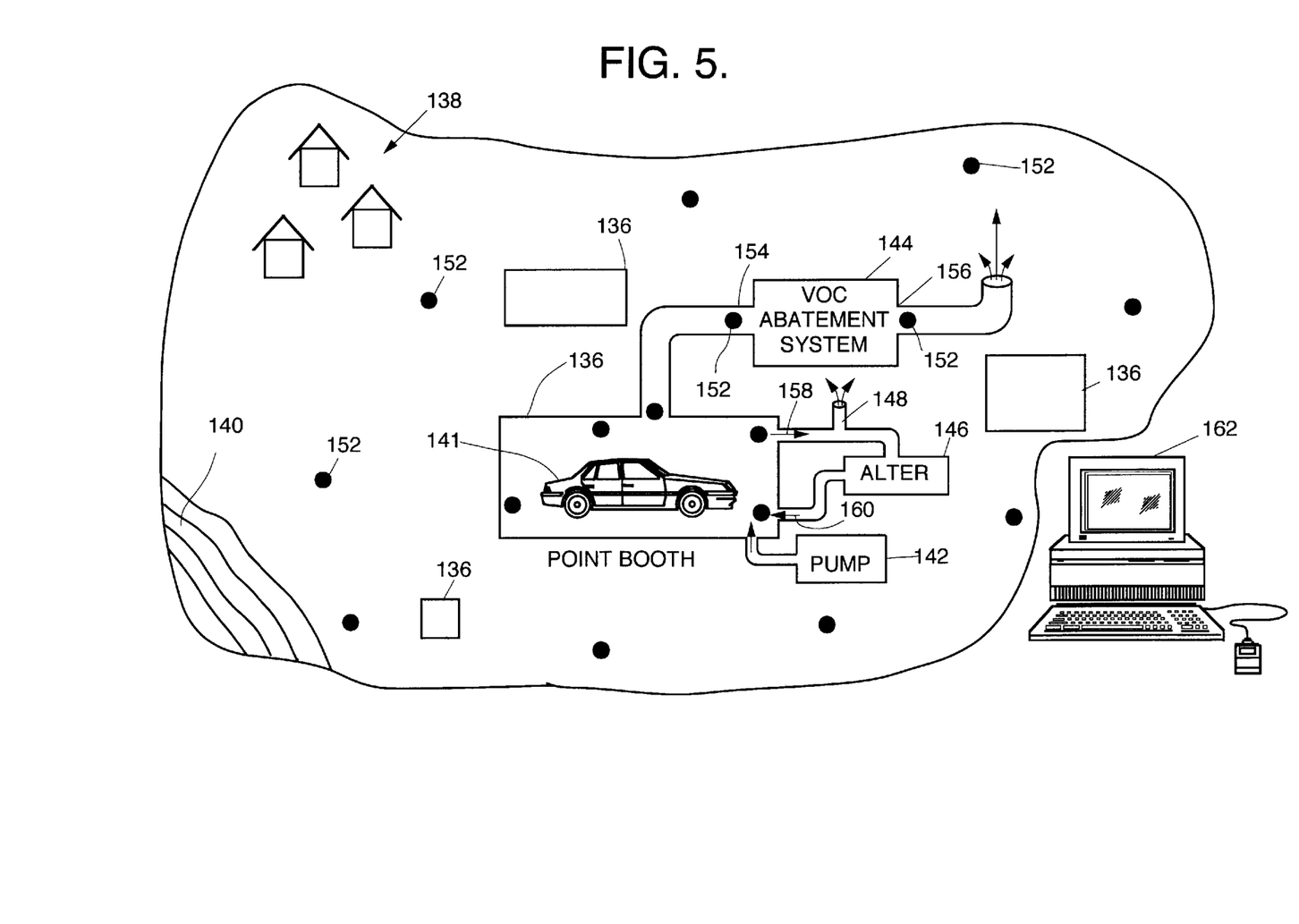
FIG. 5 is a schematic diagram of a large vehicle painting system provided with a network of vapor sensor units in accordance with the present invention.

FIG. 5 illustrates the use of the present monitoring system in an industrial painting facility. A plurality of industrial paint booths 136 are distributed over an area, which happens in this example to lie upwind from a population center 138 and a river 140. The paint booths are used to manually paint entire vehicles 141, which produces effluents that are laden with VOCs from the evaporation of paint solvents and carriers. The booths must be ventilated to protect the personnel inside the booth. However, environmental concerns and regulations forbid the direct venting of effluent VOCs to the atmosphere.

As a result, each paint booth 136 is provided with a ventilation system that includes a pump 142 that draws clean air from the atmosphere into the booth and a VOC abatement system 144 that draws contaminated air from the booth, converts and/or destroys the VOCs using, for example, an oxidation process that burns the VOCs or a process that exposes the VOCs to ultraviolet light in ozone, and then vents the cleansed air back to the atmosphere. Because the VOCs tend to settle in the bottom two-thirds of the booth, environmental regulations allow users to recirculate the air in the top one-third of the booth. This reduces the processing requirements, and thus cost, of the abatement system 144. As shown, the relatively clean air is recirculated through a filtration system 146 and then returned to the bottom of the booth. Even with the abatement and recirculation systems, the level of VOCs within the recirculation line may occasionally exceed an allowed safety threshold, in which case a bypass valve 148 opens to vent the contaminated air directly to the atmosphere rather than recirculating the VOC laden air back to the booth and exposing the personnel.

A VOC monitoring system 150 includes a plurality of sensor units 152 that are positioned a) at the inlet 154 and outlet 156 of the VOC abatement system 144, b) at the inlet 158 and outlet 160 of the recirculation system, c) inside the paint booth to measure ambient levels, d) at the bypass vent, 148 and e) around the perimeter of the area. The sensors units are networked to a central monitoring unit 162. Because of their relatively close proximity, the sensor units on the booth and the abatement equipment can be hardwired, but the sensor units around the perimeter of the area are connected via a wireless network.

The sensor units on either side of the abatement system are used to compute the composition and concentration levels of the VOCs before and after oxidation. This information is then used to control the operating parameters of the abatement system such as, in the oxidation process, the flow rate through the system, control the burn temperature, and control the burn period, which provides a safer and more efficient abatement process. The VOC composition can be resolved into different classes of VOCs such as Ketones, BTEX, Acetates, Alcohols, and Aliphatic Hydrocarbons or can be resolved to the individual species such as Xylenes, Toluene, and Ethyl Benzene in the BTEX class. The sensor units on either side of the recirculation system are used similarly to monitor the quality of the circulated air and the efficiency of the filter.

The sensor units in the booth monitor the ambient VOC level. Should the total VOC concentration exceed the safety threshold, the central monitoring unit 162 will open the bypass vent 148 to quickly reduce the ambient VOC level. Since the bypass stream vents directly tot he environment, it is essential to know what was released and in what quantity. The sensor unit at the bypass vent is used to compute the composition and concentration of the VOCs passed to the environment.

The bypass stream will form a plume that drifts in the wind toward the population center 138 and river 140. The sensor units 152 that are situated around the perimeter are used to track the progress of the plume as it moves toward the town and river. The sensor units measure the changing composition, and thus can tell whether certain components of the plume are sinking to the earth or are reacting with the atmosphere due to the presence of moisture, oxygen or sunlight. Furthermore, the sensor units measure the changing concentration, and thus can tell whether the plume is diluting to an acceptable level. This information plus current wind speed, and kinetic decomposition models for the target VOCs can be plugged into a dynamic flow model to predict what the VOC composition and concentration levels will be when the plume reaches the town and the river. This data can be critical in assessing any hazard to them. In addition, a gradient analysis can be performed on the flow data to identify which paint booth or booths are producing the VOC emissions.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

We claim:

1. A system for monitoring the composition and concentration of compounds in a fluid, comprising a plurality of sensor units distributed over an area and a central monitoring unit that communicate over a network in real-time, each said sensor unit comprising a) a power source, b) a connector that connects a sensor array to said unit, said sensor array comprising one or more sensor elements which respond to the same compound to different degrees to generate respective data signals that deviate from a baseline response in the presence of one or more compounds in the fluid, c) an interface that measures the data signals produced by each of the array's sensor elements, d) a processor that formats the data signals into an output data stream, and e) an I/O circuit that places the output data stream onto the network, said sensor units and said central monitoring unit processing in real-time the sensor units' data signals to first compute a local profile for each said sensor unit and then compute a spatial and temporal map of the compounds in the fluid over the area, said local profiles indicating whether a total concentration of the one or more compounds detected at each said sensor unit exceeds a threshold without detecting the individual compounds and their concentrations.

2. A system for monitoring the composition and concentration of compounds in a fluid, comprising a plurality of sensor units distributed over an area and a central monitoring unit that communicate over a network in real-time, each said sensor unit comprising a) a power source, b) a connector that connects a sensor array to said unit, said sensor array comprising one or more sensor elements which respond to the same compound to different degrees to generate respective data signals that deviate from a baseline response in the presence of one or more compounds in the fluid, c) an interface that measures the data signals produced by each of the array's sensor elements, d) a processor that formats the data signals into an output data stream, and e) an I/O circuit that places the output data stream onto the network, said sensor units and said central monitoring unit processing in real-time the sensor units' data signals to first compute a local profile for each said sensor unit and then compute a spatial and temporal map of the compounds in the fluid over the area, said local profiles and the spatial and temporal map including the local compositions of the compounds and their concentrations at the respective sensor units, said central monitoring unit performing a gradient analysis on the temporal map to track a path of increasing concentration leading back to a source of the compounds.

3. A system for monitoring the composition and concentration of compounds in a fluid, comprising a plurality of sensor units distributed over an area and a central monitoring unit that communicate over a network in real-time, each said sensor unit comprising a) a power source, b) a connector that connects a sensor array to said unit, said sensor array comprising one or more sensor elements which respond to the same compound to different degrees to generate respective data signals that deviate from a baseline response in the presence of one or more compounds in the fluid, c) an interface that measures the data signals produced by each of the array's sensor elements, d) a processor that formats the data signals into an output data stream, and e) an I/O circuit that places the output data stream onto the network, said sensor units and said central monitoring unit processing in real-time the sensor units' data signals to first compute a local profile for each said sensor unit and then compute a spatial and temporal map of the compounds in the fluid over the area, said local profiles and the spatial and temporal map including the local compositions of the compounds and their concentrations at the respective sensor units, said central monitoring unit comparing the composition and concentration at each said sensor unit at different times to track the flow of the compounds across the area, at least one of said sensor units further comprising a wind sensor for detecting the wind speed and direction at the sensor unit, said sensor units and the central monitoring unit using the local profiles, the flow across the area, and the wind conditions to predict the progression of the compounds across and outside the area.

4. A system for monitoring the composition and concentration of compounds in a fluid, comprising a plurality of sensor units distributed over an area to monitor the compounds' local compositions and concentrations at different points in a process that destroys the compounds and a central monitoring unit that communicate over a network in real-time, each said sensor unit comprising a) a power source, b) a connector that connects a sensor array to said unit, said sensor array comprising one or more sensor elements which respond to the same compound to different degrees to generate respective data signals that deviate from a baseline response in the presence of one or more compounds in the fluid, c) an interface that measures the data signals produced by each of the array's sensor elements, d) a processor that formats the data signals into an output data stream, and e) an I/O circuit that places the output data stream onto the network, said sensor units and said central monitoring unit processing in real-time the sensor units' data signals to first compute a local profile for each said sensor unit and then compute a spatial and temporal map of the compounds in the fluid over the area, said central monitoring unit interrelating the local compositions and concentrations to monitor the performance of the destruction process.

5. A system for monitoring the composition and concentration of compounds in a fluid, comprising a plurality of sensor units distributed around a source of compound emissions to monitor the local compositions of the compounds and their concentrations at different points and a central monitoring unit that communicate over a network in real-time, each said sensor unit comprising a) a power source, b) a connector that connects a sensor array to said unit, said sensor array comprising one or more sensor elements which respond to the same compound to different degrees to generate respective data signals that deviate from a baseline response in the presence of one or more compounds in the fluid, c) an interface that measures the data signals produced by each of the array's sensor elements, d) a processor that formats the data signals into an output data stream, and e) an I/O circuit that places the output data stream onto the network, said sensor units and said central monitoring unit processing in real-time the sensor units' data signals to first compute a local profile for each said sensor unit and then compute a spatial and temporal map of the compounds in the fluid over the area, said central monitoring unit interrelating the local compositions and concentrations to monitor the abatement of the compound emissions from the source over time.

6. A system for monitoring the composition and concentration of compounds in a fluid, comprising a plurality of sensor units distributed over an area and a central monitoring unit that communicate over a network in real-time, each said sensor unit comprising a) a power source, b) a connector that connects a sensor array to said unit, said sensor array comprising one or more sensor elements which respond to the same compound to different degrees to generate respective data signals that deviate from a baseline response in the presence of one or more compounds in the fluid, c) an interface that measures the data signals produced by each of the array's sensor elements, d) a processor that formats the data signals into an output data stream, e) an I/O circuit that places the output data stream onto the network, f) a chamber for enclosing the sensor array and a sampling mechanism for drawing compounds in the liquid into the chamber and across the sensor array and then venting the compounds out of the chamber, and g) a volume of calibration compounds, said sensor units and said central monitoring unit processing in real-time the sensor units' data signals to first compute a local profile for each said sensor unit and then compute a spatial and temporal map of the compounds in the fluid over the area, said processor causing the sensor array to be isolated in said chamber from the compounds in said fluid and then causing an amount of the calibration compounds to be released into said chamber to generate test data signals that are used to recalibrate the sensor unit.

7. An automated system for continuously monitoring the composition and concentration of volatile organic compounds (VOCs) in an atmosphere, comprising a plurality of sensor units distributed over an area, a computer and a central monitoring unit that communicate over a network in real-time, each said sensor unit comprising a) power source, b) a connector that connects a sensor array to said unit, said sensor array comprising a plurality of sensor elements which respond to the same VOC to different degrees to generate respective data signals that deviate from a baseline response in the presence of VOCs in the atmosphere, c) a chamber that encloses the sensor array, d) a vapor sampling mechanism for drawing VOCs from the atmosphere into the chamber, across the sensor array and then venting them out of the chamber, e) at least one environmental sensor for sensing environmental conditions in the chamber f) an interface that measures the data signals produced by each of the array's sensor elements, g) a processor that first compensates the data signals for the environmental conditions and then formats them into an output data stream, and h) an I/O circuit that places the output data stream onto the network, said computer determining a local VOC composition including concentrations for each said sensor unit and said central monitoring unit processing the local VOC compositions to compute the spatial and temporal composition the VOCs and their concentrations in the atmosphere over the area.

8. The system of claim 7, wherein said sampling mechanism is a passive mechanism.

9. The system of claim 7, wherein said sampling mechanism is an active mechanism, said processor controlling said sampling mechanism to draw compounds from the fluid into the chamber across the sensor array and then venting the compounds out of the chamber.

10. The system of claim 7, wherein said computer is distributed between the sensor units' processors such that each said processor first processes the compensated data signals from the sensor elements to compute the local VOC composition and then formats the local VOC composition into the output data stream that is transmitted over the network to the central monitoring unit, which then interrelates the local VOC compositions and concentration data over the area.

11. The system of claim 10, wherein said computer is included in said central monitoring unit, which first processes the compensated data signals from each of said sensor units to estimate the local VOC compositions at each said sensor unit and then interrelates the local composition and concentration data from the different sensor units over the area.

12. The system of claim 7, wherein said central monitoring unit computes a temporal map of the VOC composition over the area and performs a gradient analysis on the temporal map to track a path of increasing concentration leading back to a source of the compounds.

13. The system of claim 7, wherein said central monitoring unit computes a temporal map of the VOC composition over the area and compares the VOC composition at each said sensor unit at different times to track the flow of the VOCs across the area.

14. The system of claim 13, wherein one of said environmental sensors is a wind sensor for detecting the wind speed and direction at the sensor unit, said central monitoring unit using the local VOC compositions, the flow across the area, and the wind conditions to predict the progression of the compounds across the area and outside the area.

15. The system of claim 7, wherein said sensor units are distributed over the area to monitor the local VOC compositions at different points in a process that destroys the VOCs in the atmosphere, said central monitoring unit interrelating the local VOC compositions to monitor the performance of the destruction process.

16. The system of claim 7, wherein said sensor unit further comprises one or more environmental control mechanisms, said processor responding to the sensed environmental conditions to drive the environmental control mechanisms to maintain the environmental conditions at a baseline level.

17. A system for monitoring volatile organic compounds (VOCs) in an industrial facility, comprising:

a paint booth for painting equipment during which the evaporation of paint solvents and carriers produces VOCs that contaminate the internal atmosphere inside the paint booth;

a ventilation system for drawing air from an external atmosphere into the paint booth;

a VOC abatement system having an inlet for drawing the contaminated atmosphere from the paint booth, a mechanism for treating the contaminated atmosphere to destroy the VOCs, and an outlet for venting the treated atmosphere to the external atmosphere;

a bypass vent for selectively venting the contaminated atmosphere in the paint booth directly to the external atmosphere;

a data communications network;

a plurality of sensor units for detecting VOCs including a first sensor unit positioned in the paint booth, a second sensor unit positioned near the bypass vent, a third sensor unit positioned at the inlet to the abatement system, and a fourth sensor unit positioned at the outlet to the abatement system, each said sensor unit comprising a) power source, b) a connector that connects a sensor array to said unit, said sensor array comprising a plurality of sensor elements that respond to the same VOC to different degrees to generate respective data signals in the presence of VOCs, c) an interface that measures the data signals produced by each of the array's sensor elements, d) a processor that formats the data signals into an output data stream, and e) an I/O circuit that places the output data stream onto the network;

a computer connected to said network that computes an ambient VOC level in the paint booth at the first sensor unit, a bypassed VOC level at the second sensor unit, an intake VOC level at the third sensor unit, and a discharged VOC level at the outlet of the VOC abatement system, said VOC levels including a composition of VOCs and their concentrations; and a central monitoring unit in said network that a) processes the intake and outlet VOC levels to monitor the performance of the VOC abatement system and, if necessary, takes corrective action to restore its performance and b) monitors the ambient VOC level and, when it exceeds a threshold level, opens the bypass vent to vent the contaminated atmosphere to the external atmosphere and records the bypassed VOC level.

18. The system of claim 17, wherein said computer is distributed among the sensor units' processors such that each said processor first processes the data signals from the sensor elements to compute the VOC level and then formats it into the output data stream that is transmitted over the network to the central monitoring unit.

19. The system of claim 17, wherein said computer is included in said central monitoring unit, which first processes the data signals from each of said sensor units to compute the VOC levels at each said sensor unit and then processes them to monitor the abatement system and the ambient VOC level.

20. The system of claim 17, wherein each said sensor unit further comprises a chamber for enclosing the sensor array and a sampling mechanism for drawing the contaminated atmosphere into the chamber, across the sensor array and then venting the contaminated atmosphere out of the chamber.

21. The system of claim 20, wherein said sensor unit comprises one or more environmental sensors for sensing environmental conditions in the chamber, said processor compensating for the environmental conditions so that the measured data signals are approximately independent of those conditions.

22. The system of claim 21, wherein said sensor unit further comprises one or more environmental control mechanisms, said processor responding to the sensed environmental conditions to drive the environmental control mechanisms to maintain the environmental conditions at a baseline level.

23. The system of claim 17, wherein the VOC abatement system's mechanism destroys the VOCs, said central monitoring unit taking corrective action by adjusting the operating parameters of the abatement system.

24. The system of claim 17, wherein the composition of VOCs includes the Ketones, BTEX, Acetates, Alcohols, and Aliphatic Hydro-Carbon classes of VOCs, said central monitoring unit comparing the concentrations of these VOC classes at the intake and outlet of the VOC abatement system to monitor the system's performance.

25. The system of claim 24, wherein the computer identifies the different species in each VOC class and their respective concentrations.

26. The system of claim 17, wherein venting the contaminated atmosphere directly to the external atmosphere through the bypass vent creates a plume, a plurality of said sensor units being positioned outside the paint booth to monitor the VOC levels in the external environment, said central monitoring unit computing a temporal map of the VOC levels over an area outside the paint booth and comparing the VOC levels at each said sensor unit at different times to track the progression of the plume across the area.

27. The system of claim 26, wherein at least one of the sensor units outside the paint booth detects the wind speed and direction, said central monitoring unit using the VOC levels at the sensor units outside the paint booth, the bypassed VOC level, the progression of the plume across the area, and the wind conditions to predict the progression of the VOCs across and outside the area.

28. The system of claim 26, further comprising a plurality of similar paint booths that are positioned at different locations in the area, said central monitoring unit performing a gradient analysis on the temporal map to track a path of increasing concentration leading back to the one or more of said paint booths that are the source of the VOC plume.

\* \* \* \* \*